US012472521B2

(12) United States Patent
Jung et al.

(10) Patent No.: US 12,472,521 B2
(45) Date of Patent: Nov. 18, 2025

(54) LIQUID DISPENSER WITH TWO LIQUID RESERVOIRS

(71) Applicant: Aptar Radolfzell GmbH, Radolfzell (DE)

(72) Inventors: Timo Jung, Radolfzell (DE); Hubertus Pfeffer, Eigeltingen (DE); Lenz Schmid, Constance (DE)

(73) Assignee: APTAR RADOLFZELL GMBH, Radolfzell (DE)

( * ) Notice: Subject to any disclaimer, the term of this patent is extended or adjusted under 35 U.S.C. 154(b) by 256 days.

(21) Appl. No.: 18/190,293

(22) Filed: Mar. 27, 2023

(65) Prior Publication Data

US 2023/0302475 A1 Sep. 28, 2023

(30) Foreign Application Priority Data

Mar. 28, 2022 (EP) .................................... 22164746

(51) Int. Cl.
*B05B 11/10* (2023.01)
*A61M 35/00* (2006.01)

(52) U.S. Cl.
CPC ....... *B05B 11/1084* (2023.01); *A61M 35/003* (2013.01); *B05B 11/1001* (2023.01); *B05B 11/1052* (2023.01)

(58) Field of Classification Search
CPC ............. B05B 11/1084; B05B 11/1001; B05B 11/1052; B05B 11/0078; B05B 11/0097; B05B 15/30; B05B 11/0056; A61M 35/003
See application file for complete search history.

(56) References Cited

U.S. PATENT DOCUMENTS

| | | | |
|---|---|---|---|
| 4,773,562 A | 9/1988 | Gueret | |
| 5,169,029 A | 12/1992 | Behar et al. | |
| 5,301,841 A * | 4/1994 | Fuchs | B05B 11/0038 222/135 |
| 5,623,974 A | 4/1997 | Losenno et al. | |

(Continued)

FOREIGN PATENT DOCUMENTS

| | | |
|---|---|---|
| CN | 214650011 U | 11/2021 |
| CN | 214876887 U | 11/2021 |

(Continued)

OTHER PUBLICATIONS

European Search Report issued in corresponding European Application No. 22164746.4, with English translation of categories of cited documents, dated Sep. 1, 2022 (14 pages).

*Primary Examiner* — Vishal Pancholi
(74) *Attorney, Agent, or Firm* — FLYNN THIEL, P.C.

(57) ABSTRACT

A liquid dispenser for dispensing a cosmetic or pharmaceutical liquid produced by mixing two starting liquids. The liquid dispenser has at least two liquid reservoirs for holding the two starting liquids and a discharge opening, and at least one pump device by which liquid can be delivered from the liquid reservoirs to the discharge opening. The dispenser has one intake opening for removing the liquid, via the at least one pump device, at one end of each liquid reservoir, and one intake tube extending from the intake opening to a bottom end of each liquid reservoir. Further, one filling opening is provided at the bottom end of each of the liquid reservoirs.

7 Claims, 8 Drawing Sheets

(56) References Cited

U.S. PATENT DOCUMENTS

| | | | | |
|---|---|---|---|---|
| 5,833,121 | A * | 11/1998 | Gueret | B05B 11/0029 222/144.5 |
| 10,675,647 | B2 | 6/2020 | Kim et al. | |
| 2001/0025859 | A1 | 10/2001 | Dumont | |
| 2006/0065674 | A1 | 3/2006 | Lasserre et al. | |
| 2013/0161351 | A1 | 6/2013 | Eini et al. | |
| 2016/0023228 | A1 | 1/2016 | Scott et al. | |
| 2016/0199864 | A1 | 7/2016 | Quennessen | |

FOREIGN PATENT DOCUMENTS

| | | | |
|---|---|---|---|
| DE | 202004010515 | U1 | 12/2004 |
| WO | 2021093972 | A1 | 5/2021 |

* cited by examiner

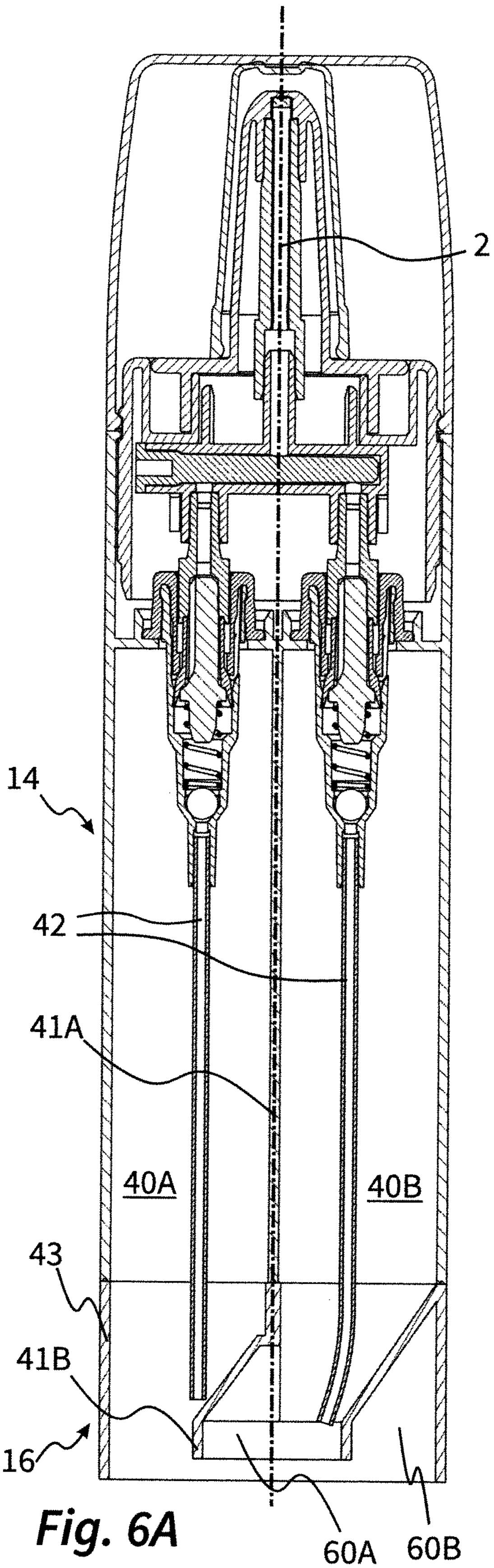
Fig. 6A
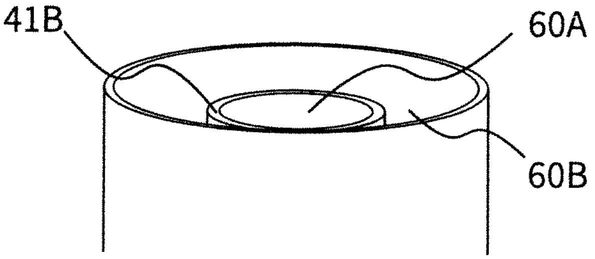
Fig. 6B
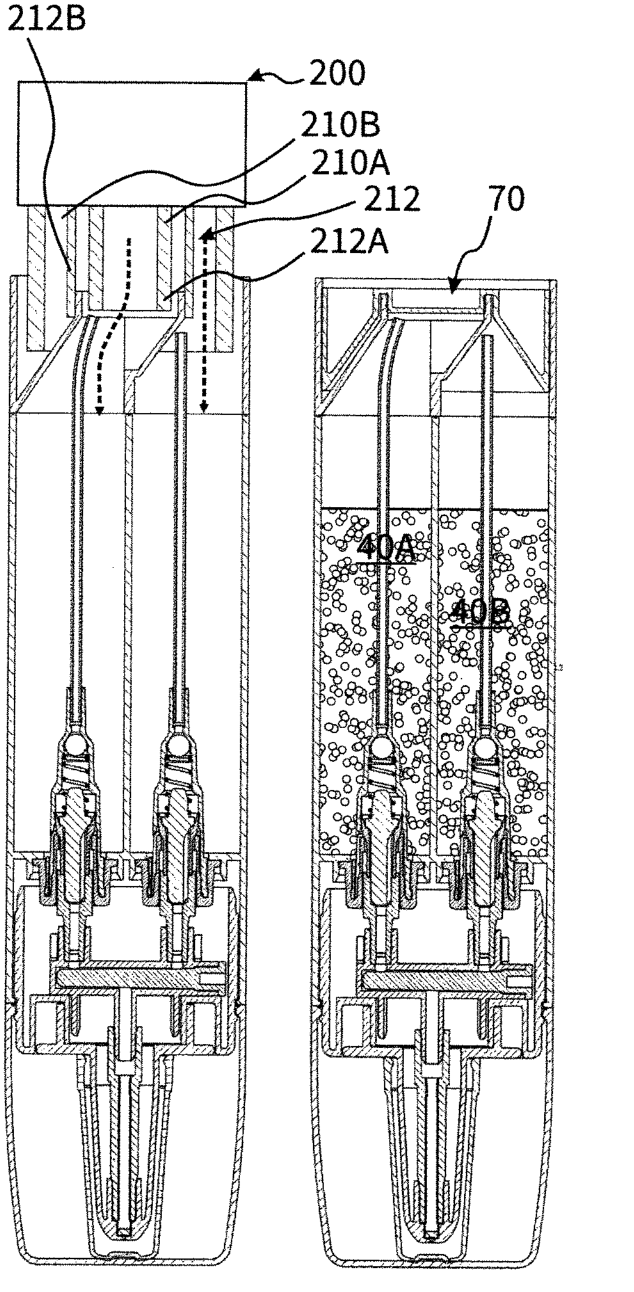
Fig. 6C
Fig.6D

LIQUID DISPENSER WITH TWO LIQUID RESERVOIRS

CROSS-REFERENCE TO RELATED APPLICATION

This claims priority from European Application No. 22164746.4, filed Mar. 28, 2022, the disclosure of which is hereby incorporated by reference in its entirety.

FIELD OF APPLICATION AND PRIOR ART

The invention relates primarily to a liquid dispenser for discharging an in particular pharmaceutical or cosmetic liquid which is produced by mixing two or more starting liquids. In the case of a generic liquid dispenser, it is provided that it has an independent liquid dispenser for each of the starting liquids. Separate storage of the starting liquids until the time they are discharged can be offered, depending on the starting liquids, because the direct storage of the ready-mixed liquid in a common liquid dispenser would impair its quality.

In the case of a generic liquid dispenser, the starting liquids are delivered in the course of the discharge by a common pump device or by separate pump devices to a discharge opening and are mixed with each other in the process.

Production of a liquid dispenser with more than one liquid reservoir makes it harder to fill the liquid dispenser. In practice, it is problematic to fill a reservoir component with two liquid reservoirs and then to install the pump devices and/or the discharge head thereon.

OBJECT AND SOLUTION

One object of the invention is to propose a liquid dispenser of the generic type which allows filling in an advantageous fashion. The object is furthermore to propose a filling method suitable therefor.

Proposed is a liquid dispenser for dispensing a cosmetic or pharmaceutical liquid which is produced by mixing two starting liquids.

This liquid dispenser usually has, in the already described fashion, at least two liquid reservoirs for holding the two starting liquids. The liquid reservoirs define a main direction of extent of the liquid dispenser. The walls of the liquid reservoirs are in particular preferably designed cylindrically, at least partially, relative to the main direction of extent.

The liquid reservoirs are preferably formed at least primarily by one or each main reservoir body which isolates the liquid reservoirs relative to the surroundings. At least one partition wall is provided between the liquid reservoirs such that the starting liquids in the liquid reservoirs do not mix with each other. In the case of a structure in which two separate main reservoir bodies each predominantly define a liquid reservoir, at least two partition walls are provided between the liquid reservoirs.

A liquid dispenser according to one aspect of the invention has at least one discharge opening through which the mixed liquid is discharged. Designs in which separate discharge openings are provided and the liquids are mixed only downstream from the discharge openings during the application are also conceivable.

The liquid dispenser according to on aspect of the invention furthermore has at least one pump device by means of which liquid is delivered from the liquid reservoirs to the discharge opening. Each liquid reservoir is preferably provided with an independent pump device, these at least two pump devices in particular preferably, however, being mechanically coupled such that they are always simultaneously activated at least intermittently. The two outlet sides of the preferably at least two pump devices are preferably connected to a common mixing duct in which the starting liquids are brought together.

The liquid dispenser preferably has a push actuator which can be displaced relative to the liquid reservoirs separately from the discharge opening or together with the discharge opening. The at least one pump device is coupled thereto in such a way that the displacement of the push actuator causes activation of the pump device.

In order to remove the liquid from the liquid reservoirs, a respective intake opening, through which liquid can be drawn to the pump device, is provided at a respective top end which is provided on the same side as the at least one pump device and the at least one discharge opening. A respective intake tube which extends as far as the opposite bottom end of the liquid reservoir is provided at these at least two intake openings.

The use of the liquid dispenser takes place in an orientation in which the bottom end of the liquid reservoir faces downwards and the top end faces upwards. The starting liquids are drawn out of the liquid reservoirs by means of the pump devices, wherein the intake tubes which project freely from the extraction openings into the liquid reservoirs and are consequently surrounded by liquid cause the liquid to be removed from the bottom end of the liquid reservoir.

In a liquid reservoir according to one aspect of the invention, it is provided that the liquid reservoir is filled in an inverted position with an upward facing bottom end of the liquid reservoir. For this purpose, a respective filling opening is provided in a base region of the liquid reservoir at the bottom end.

This type of filling has been proved to offer considerable advantages. A dispenser according to the invention can thus be completely assembled, apart from a reservoir base component or stopper, before the filling takes place.

The filling opening can be formed by the common main reservoir body being still open at its bottom end during the filling such that the liquid can be introduced through these open bottom ends of the at least two liquid reservoirs and the open ends can then be closed by means of a common stopper or by means of separate stoppers or by means of a reservoir base component.

It is advantageous if the liquid reservoirs have a reservoir base in the base region, wherein the reservoir bases of both liquid reservoirs are preferably formed by a common reservoir base component which is connected to the said main reservoir body in particular preferably in a liquid tight manner. In particular, the reservoir base component or the reservoir base components can be connected in a liquid tight manner to the main reservoir body by being adhesively bonded or welded. A simple press-fit can also be sufficient, wherein for this purpose the main reservoir body preferably ends in each case in a round opening into which the reservoir base components with a correspondingly round outside are pushed.

In the case of a design with one or more reservoir base components, the filling openings are preferably designed as perforations in this preferably common reservoir base component.

The reservoir base can preferably serve the purpose of holding the respective intake tube in a position which, when the liquid reservoirs are filled with the starting liquids, prevents a corresponding filling needle from colliding with the intake tubes.

For this purpose, it is considered to be particularly advantageous if the reservoir bases each have a holding geometry by means of which a bottom end of the respective intake tube is kept away from the respective filling opening. The reservoir base extends for this purpose so far in the direction of the top end of the liquid reservoir that it projects into the region of the respective intake tube and mechanically keeps it at a distance from the filling opening. In particular, the filling opening which perforates the reservoir base can have a supporting wall which surrounds the respective filling opening. The intake tube is arranged at the level of the supporting wall, offset relative to the filling opening transversely to the main direction of extent and is consequently arranged outside the supporting wall. Because of the supporting wall, it cannot pass into the region of the filling opening.

The reservoir bases are preferably each provided with oblique guide surfaces at least in some places. By virtue of these, the intake tubes can be pushed away from the respective filling opening during the assembly of the liquid dispenser, in particular during the attachment of the correspondingly designed reservoir base component.

Alternatively or additionally, it can be provided that barrier sections, which are arranged inside the respective liquid reservoir so that they are aligned with the respective filling openings and are thus arranged longitudinally or along the main direction of extent between the filling openings and the intake openings, are provided in the base region of the liquid reservoirs. An essentially straight or slightly curved intake tube can thus not project into the filling opening and instead is kept away from it by the barrier section. An upper side of the barrier sections is preferably provided with an oblique plane or with an upward tapering shape in order to push the intake tube to one side during the installation of the reservoir base onto the liquid reservoir.

In order to promote simple production of the plastic individual parts, the barrier sections can be formed by inserts which are separate from the reservoir base component and are fastened to the reservoir base component, in particular in the filling openings by means of a clamped or latched connection.

A further possible design for fixing the position of the intake tube and positioning it away from the filling opening provides that the intake tube is secured in particular in the region of an outer wall of the liquid dispenser by means of a supporting means spaced apart from the intake opening. The supporting means can be provided, for example, on the inner side of the outer wall.

The intake tube can be effectively kept away from the filling opening by the barrier sections and the described design of the reservoir base and by the supporting means on the outer wall. In particular, this allows the intake opening to which the intake tube is attached and the filling opening to be provided in an aligned arrangement relative to the main direction of extent. This is advantageous in particular in the case of slim elongated liquid dispensers.

If the shape of the liquid reservoir allows it, it can, however, be advantageous to arrange the intake openings so that they are offset relative to the filling openings with respect to the main direction of extent. In the case of a straight intake tube which extends downwards in a straight line from the intake opening, it can consequently be effected or facilitated that the intake tube does not pass into the region of the filling opening and consequently make the filling process harder.

After filling, the filling openings are closed, preferably by means of stoppers which are pressed into the filling openings. The filling openings are preferably round and as a result this facilitates leaktight closure. The at least two stoppers are preferably formed by a common stopper component.

It can be provided to hold the filling openings already closed by means of a temporary stopper in a state before the filling. Such a temporary stopper can keep an interior of the liquid reservoir sterile during handling. The temporary stoppers can be pushed into the respective liquid reservoir from outside in order then to be able to carry out the filling.

The temporary stoppers are preferably designed as a single piece and in particular are attached to a surrounding wall of the respective filling opening preferably by means of a film hinge. Alternatively, the filling openings can be closed before filling by a thin membrane which may be integral with the surrounding wall and is perforated before or during the introduction of the filling nozzles.

In preferred designs of the dispenser with two liquid reservoirs, the latter are arranged so that they are situated next to each other at least in an upper region, i.e. such that neither of the two liquid reservoirs completely surrounds the other with respect to the cross-section.

It can, however, be provided that the second liquid reservoir surrounds the first liquid reservoir at least in a base region of the liquid reservoir, i.e. is provided circumferentially on all sides of the inner first liquid reservoir. The partition wall between the liquid reservoirs is then designed in the base region as an annular partition wall which surrounds a first filling opening of the first liquid reservoir and which is surrounded by a second filling opening of the second liquid reservoir. This concentric arrangement of the filling openings allows the liquid reservoirs to be filled whatever the rotated position.

The described concentric arrangement of the liquid reservoirs is preferably restricted to the base region, wherein the liquid reservoirs are arranged next to each other in the manner described in an upper region. A transfer wall structure, which transfers the non-annular partition wall in the upper region into the annular partition wall in the base region is provided in a transition region.

In order to ensure that the intake tube assumes in the base region a position which is unproblematic for the filling process, it can also be provided that a lower subsection of the intake tube is firmly connected to a reservoir base component. The intake tube or a part thereof is in this case already fastened to the reservoir base component or is an integral part thereof before the latter is installed.

The intake tube is joined to the intake opening or a part of the intake tube there during installation. Guide surfaces on the base, for example with an inner or outer funnel structure, for the guided placement of the intake tube onto the intake opening are preferably provided on the intake tube. The guide surfaces are preferably provided on a plurality of individual ribs in the form of lead-in slopes.

The above described structure of the liquid reservoirs is provided in particular for dispensers with two liquid reservoirs. It can, however, also be used with dispensers with three or more liquid reservoirs and preferably the same number of pump devices. The aspects of the invention mentioned with respect to the structure of the liquid dispensers furthermore also extend to dispensers with just one liquid reservoir.

In addition to the described dispenser, the invention also comprises a method for producing and in particular filling a liquid dispenser. The liquid dispenser has in the manner already described above at least two liquid reservoirs, for each of which a filling opening is provided in the base region of the liquid reservoirs. The liquid reservoirs are preferably provided in the above described manner with a design in which the intake tube does not project into the region of the filling opening.

The liquid reservoirs are filled with an orientation of the liquid dispenser in which the filling openings face upwards and accordingly a discharge opening and/or a push actuator face downwards. A filling head with two or correspondingly more filling nozzles is provided which simultaneously or successively enter the filling openings of the dispenser and there dispense the respective starting liquid. The liquid reservoirs are thus filled. The liquid reservoirs are then closed by means of stoppers or by means of a closed reservoir base component.

A reservoir base component in which the at least one filling opening is provided has preferably already been attached to a main reservoir body during the installation of the dispenser and before it is filled, at least one intake tube of the liquid reservoir having been pushed away from the at least one filling opening by the reservoir base component in the course of this attachment.

In the case of a design of the filling opening with a concentric arrangement, the filling is preferably effected by means of a filling head which has an inner filling nozzle and an outer filling nozzle, wherein the inner filling nozzle is arranged inside the outer filling nozzle. The inner filling nozzle is preferably separated from a liquid-guidance region of the outer filling nozzle by a double-shell intermediate wall. An outer shell of the intermediate wall is arranged outside the annular partition wall of the liquid reservoirs during the filling and an inner shell of the intermediate wall is arranged inside this partition wall during the filling.

As well as the structure of the reservoir base, a special design of the filling nozzles used can also ensure that an intake tube does not obstruct the filling process. For this purpose, it is provided that the liquid is dispensed through at least one lateral outlet opening provided on the side of the filling nozzle. The shape of the filling nozzle with a displacement geometry at its distal end face preferably causes the intake tube, when it enters the filling opening, to slide on the end face, in particular preferably away from the lateral outlet opening.

In the filled state, the liquid reservoirs are filled with starting liquids which, when mixed, form a cosmetic or pharmaceutical liquid, which can, in particular, be a formulation which contains nitrogen oxide (NO).

BRIEF DESCRIPTION OF THE DRAWINGS

Further advantages and aspects of the invention can be found in the claims and the following description of preferred exemplary embodiments of the invention which are explained below with the aid of the Figures.

FIGS. 6A to 6D show a liquid dispenser according to a fifth exemplary embodiment of the invention.

DETAILED DESCRIPTION OF THE EXEMPLARY EMBODIMENTS

Figure 1:
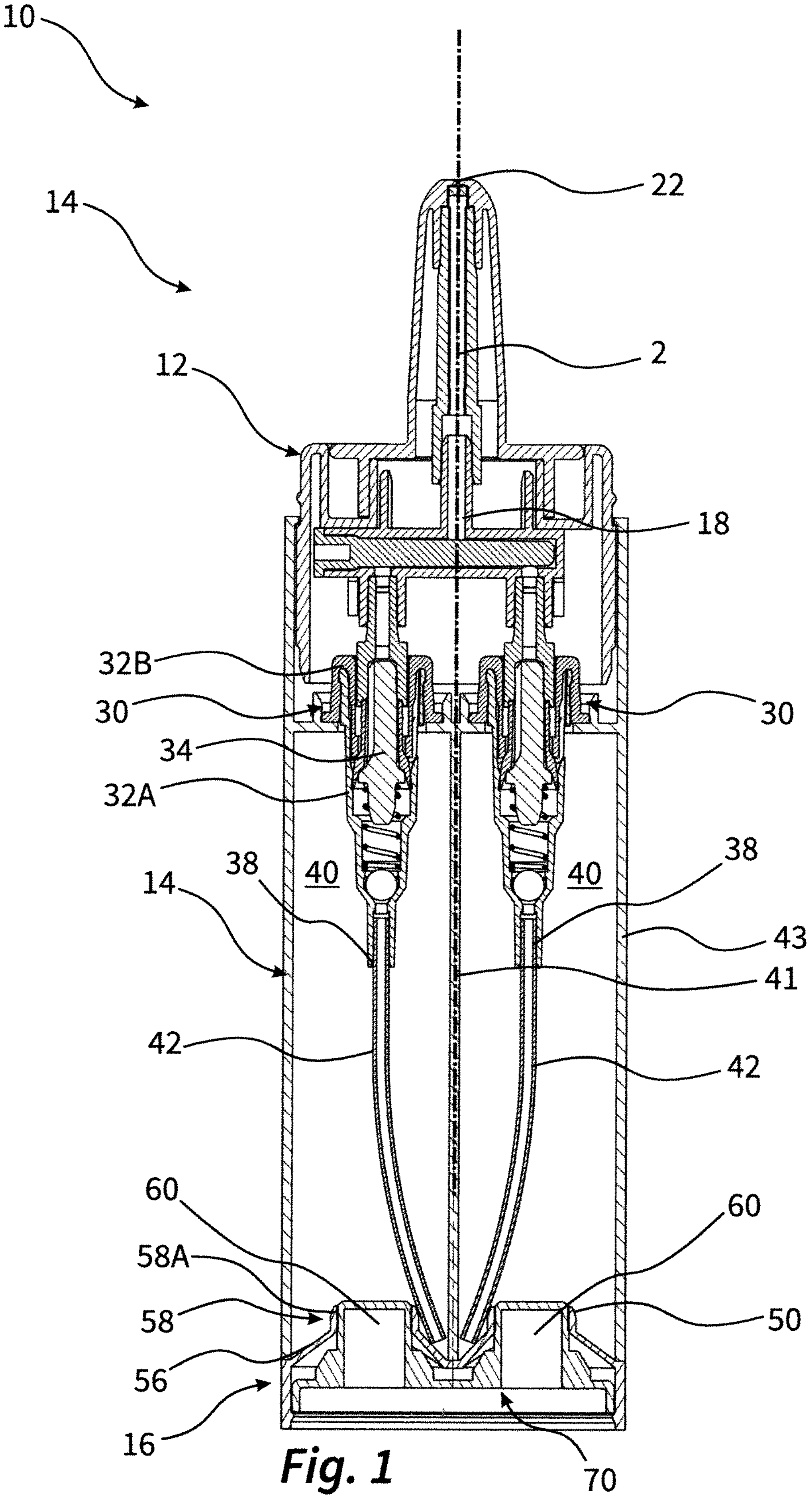
FIG. 1 shows a first exemplary embodiment of a liquid dispenser according to the invention in an overall view.

FIG. 1 shows a liquid dispenser 10 which is designed to dispense a liquid which is produced from two starting liquids by being mixed in the course of the discharging. The liquid dispenser 10 is oriented along a main direction of extent (or longitudinal axis) 2 of the liquid dispenser 10, and has at its top end a discharge opening 22 through which liquid can be dispensed. This liquid is supplied to the discharge opening 22 through a discharge duct 18. The discharge duct 18 is fed by two pump devices 30.

In order to activate the pump devices 30, the liquid dispenser has a push actuator 12 which acts on piston components 34 of both pump devices 30 and therefore activates them simultaneously. As a result, liquid is pushed in the direction of the discharge opening 22 from the pump chambers of the pump devices.

The pump devices 30 are designed to deliver liquid from two elongated liquid reservoirs 40. They are each fastened by means of an upper pump housing part 32B to an intermediate wall closing the liquid dispenser 40 at the top. The pump devices 30 extend with a lower pump housing component 32A into the liquid reservoirs 40. Respective intake openings 38 are provided at the bottom end of the pump devices 30, wherein an intake tube 42, which extends into a base region of the liquid reservoirs 40, is in each case attached to these intake openings 38. The purpose of these intake tubes 42 is to draw liquid from the bottom end of the liquid reservoirs such that the dispenser 10 can be used in the orientation illustrated in FIG. 1 and liquid can be discharged.

The liquid reservoirs 40 are delimited primarily by a main reservoir body 14 which predominantly forms both an outer wall 43 and a partition wall 41. A reservoir base 50 is provided at the bottom end of the liquid dispenser 10 in order to close the main reservoir body 14, wherein it is formed in the present case by a separately produced reservoir base component 16 which is connected to the main reservoir body 14, for example, by means of a welded connection, a press-fit connection or an adhesively bonded connection.

The reservoir base 50 has two filling openings 60 which, in the state in FIG. 1, are already closed by means of a stopper component 70. The reservoir base 50 furthermore has a holding geometry 58, in particular formed by supporting walls 58A which extend so far upwards that the intake tubes 42 can consequently be kept away from the filling openings 60. It can be clearly seen in FIG. 1 that the intake tubes 42 are pushed away from the filling openings 60 by the supporting walls 58A. Oblique guide surfaces 56 on the reservoir base 50 ensure that the intake tubes 42 are pushed away from the filling openings 60 during installation of the reservoir base 50 to the main reservoir body 14.

This design of the reservoir base which is capable of ensuring the position of the bottom ends of the intake tubes serves to facilitate the filling of the liquid dispenser 10.

Figures 2A, 2B, 2C:
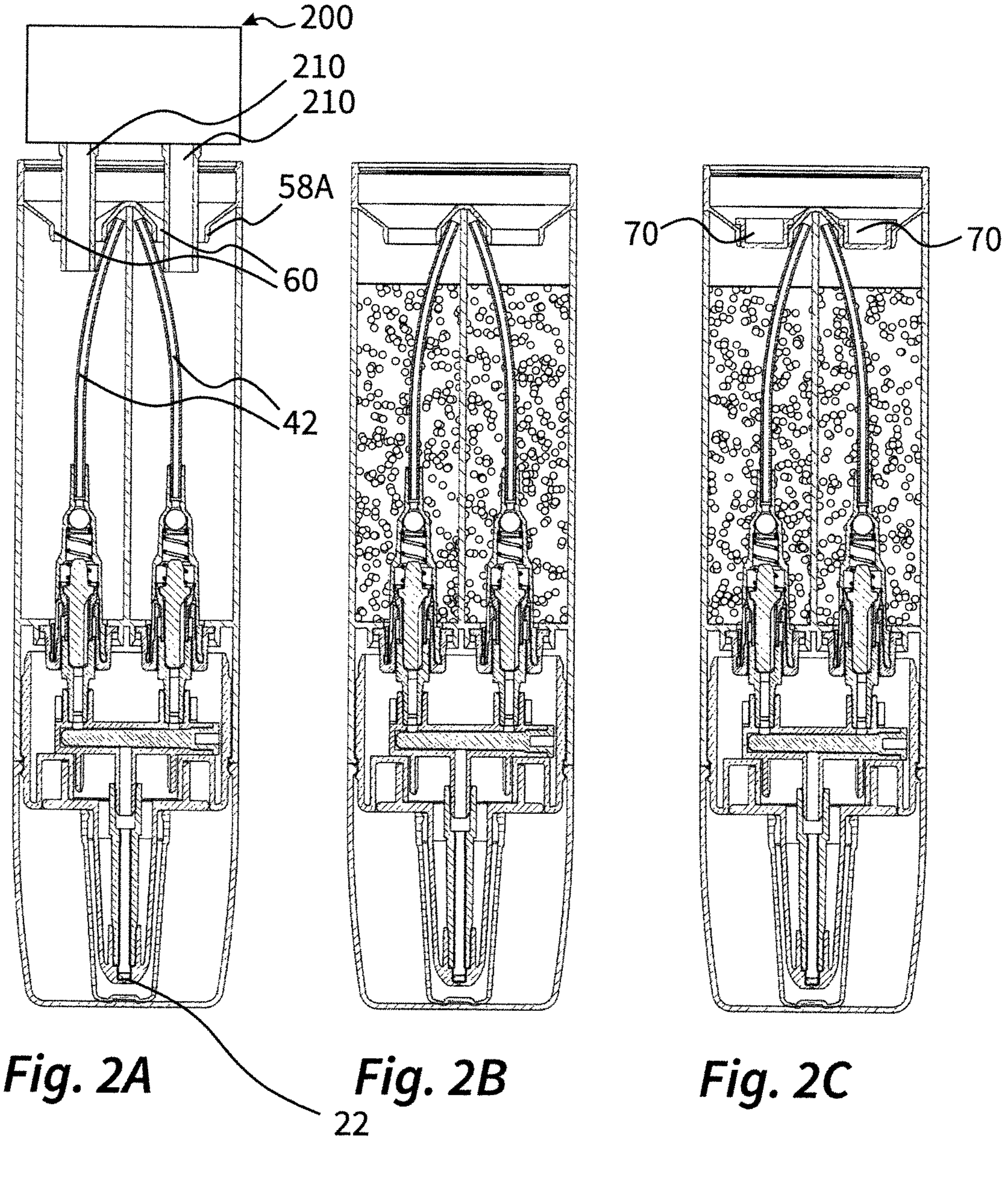
FIGS. 2A-2C show the liquid dispenser in FIG. 1 during filling.

The filling process is illustrated in FIGS. 2A to 2C. As is clear from FIG. 2A, in the case of a liquid dispenser 10 according to the invention, the filling process takes place in a position in which the discharge opening 22 faces downwards and the filling openings 60 on the base face upwards. FIG. 2A shows the liquid dispenser 10 in this orientation with filling nozzles 210, which are part of a common filling head 200, already inside. The filling nozzles 210 project through the filling openings 60 into the liquid reservoirs 40, wherein fixing the position of the intake tubes 42 by means of the supporting walls 58A means that they do not obstruct the filling process.

FIG. 2B shows the filled state of the liquid reservoirs 40. Once this state has been achieved, the filling head 200 is withdrawn and stopper components 70 are pushed into the filling openings 60. The filling openings 60 are preferably circular such that reliable sealing can be obtained by pressing in the stopper components 70. It is considered to be advantageous if the liquid reservoirs can be closed after filling using simple installation techniques, in particular without adhesive bonding or welding of components. This reduces the effort required to close the liquid reservoirs 40 at the filling point.

In the state in FIG. 2C, the liquid dispenser 10 is completed and filled and thus in a state in which it is ready to be sold.

Figure 3:
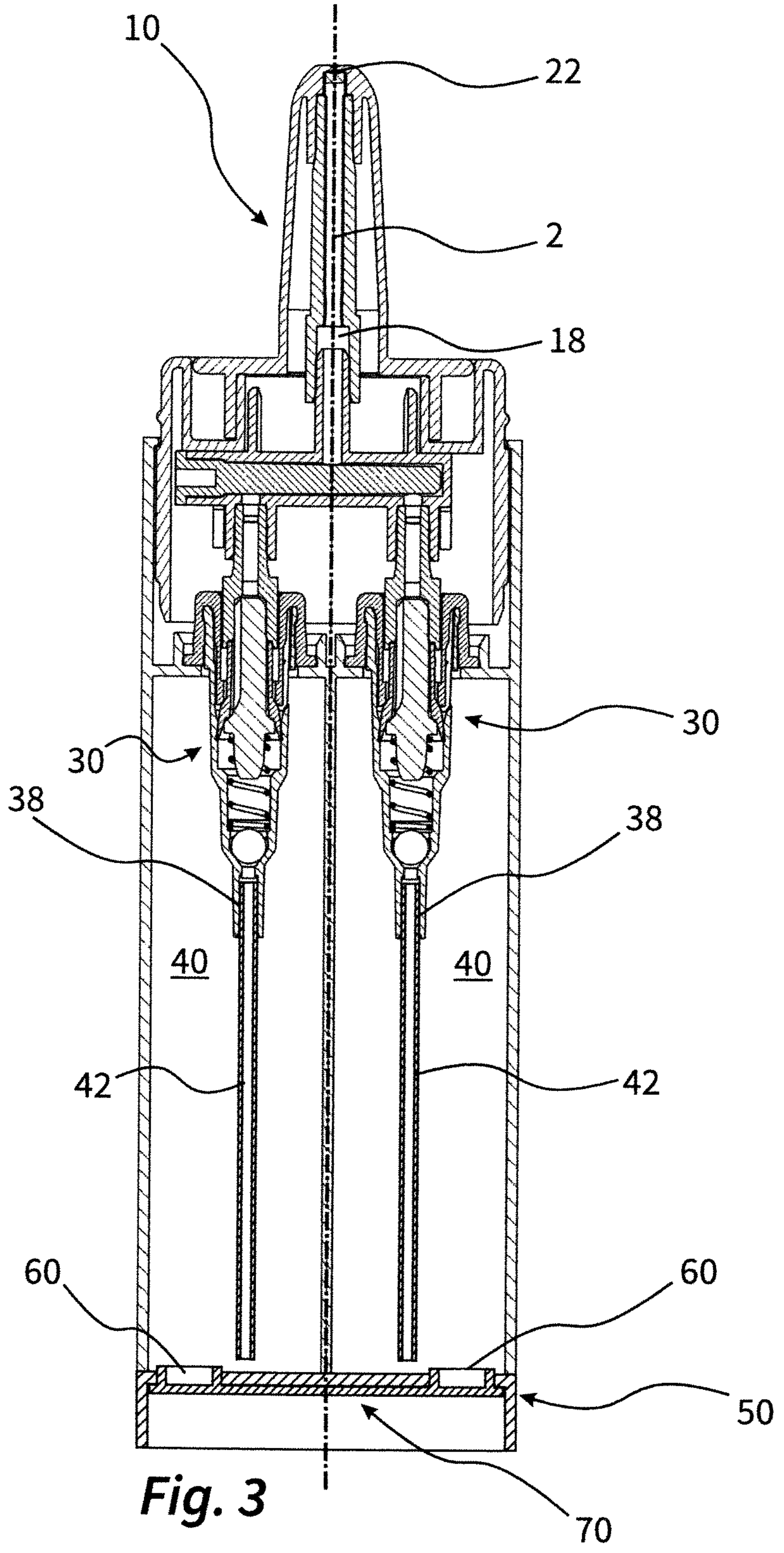
FIG. 3 shows a liquid dispenser according to a second exemplary embodiment of the invention.

FIG. 3 shows another design of a liquid dispenser 10. As is also the case for the other already described designs of the liquid dispenser 10, the discharge mechanism with the two pump devices 30 and the discharge duct 18 which leads to the discharge opening 22 is in each case unchanged. In the design in FIG. 3, as distinct from the design in FIGS. 1 and 2, it is not provided that the reservoir base 50 keeps the intake tubes 42 away from the filling openings 60 in a mechanical fashion. Instead, it is provided that the filling openings 60 are arranged so that they are offset relative to the intake openings 38 of the pump devices 30 with respect to the main direction of extent 2. If intake tubes with a sufficient inherent stability are used, it can in this way be ensured that the filling nozzles 210 do not collide with the intake tubes 42 during the filling of the liquid reservoirs 40.

Figure 4A:
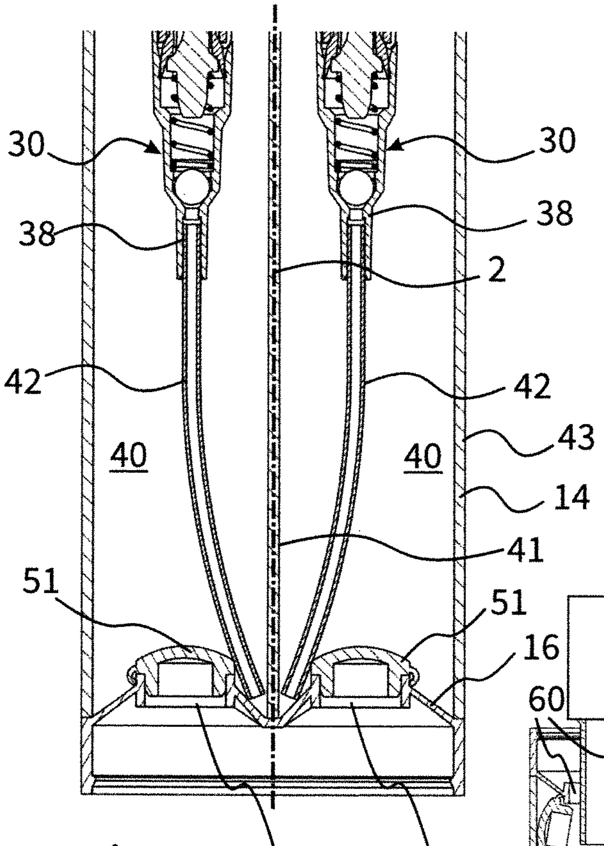
FIGS. 4A to 4C show a third exemplary embodiment in an overall view and the sequence during filling.
Figure 4B:
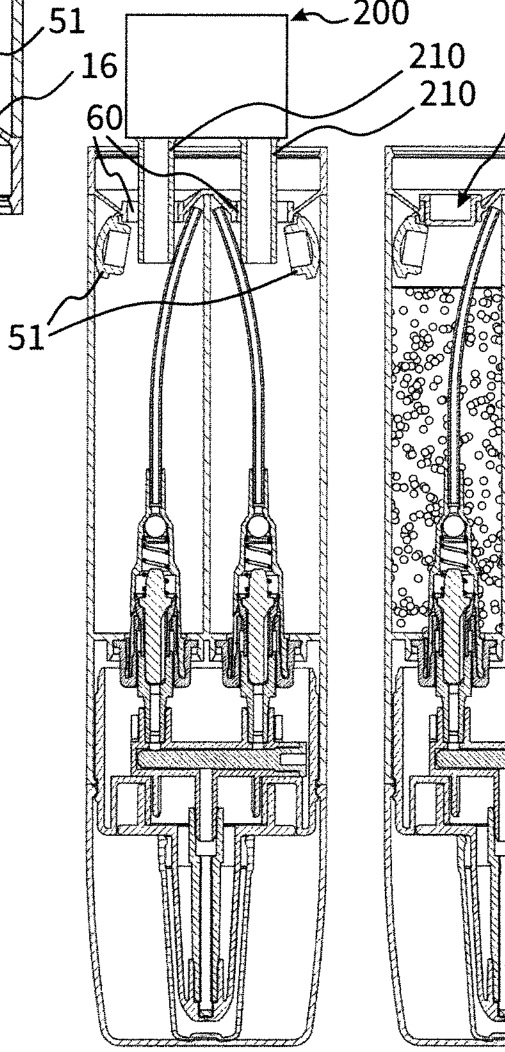
Figure 4C:
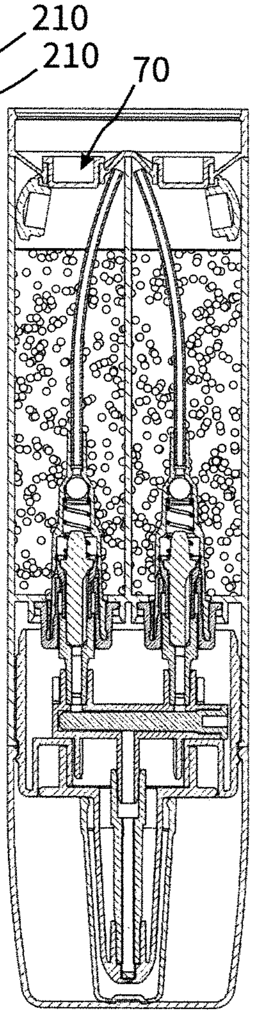

The design in FIGS. 4A to 4C is in turn very similar to that in FIGS. 1 to 2C. A distinctive feature consists in the filling openings 60 being closed by temporary stoppers 51 before the liquid reservoirs 40 are filled. The latter are connected to the reservoir base component 16 by means of a film hinge in the exemplary embodiment in FIGS. 4A to 4C.

The stoppers 51 ensure that the interior of each of the liquid reservoirs 40 is insulated with respect to the surroundings during the handling of the still empty liquid dispensers 10 and hence can be kept sterile.

Only when the filling head 200 enters the filling openings 60 with the filling nozzles 210 during filling in the manner illustrated in FIG. 4B are the temporary stoppers 51 pushed out of the filling openings 60 and does the filling then begin.

After the filling has ended, other stopper components 70 are inserted into the filling openings in the manner illustrated in FIG. 4C. Even though two separate stopper components 70 are used in the Figure, it is also possible for a common stopper component 70 to close both filling openings 60, corresponding to FIG. 1.

FIGS. 5A to 5D show a further structure of a dispenser 10. It is provided here that the reservoir base 50 is provided in the region of the filling openings 60 with barrier sections 52 which cover the filling openings 60 and which have a tapering shape on their upper side. In the present case, the barrier sections 52 are provided as separate inserts 54 which are inserted into the filling openings 60 of the reservoir base component 16 in particular in clamping fashion. A one-piece design would, however, alternatively also be possible.

Figure 5A:
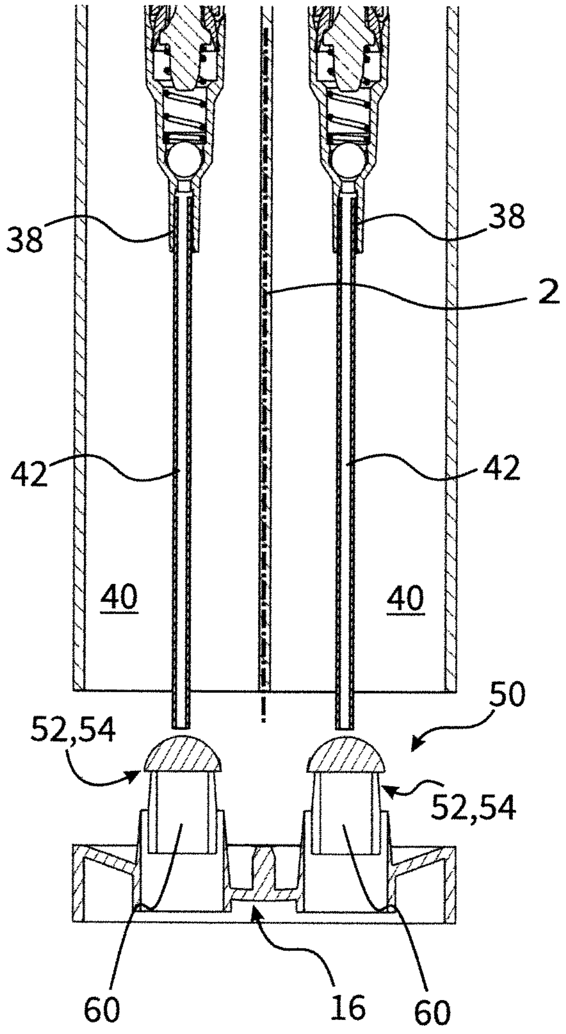
FIGS. 5A to 5D show the installation and filling of a liquid dispenser according to a fourth exemplary embodiment of the invention.
Figure 5B:
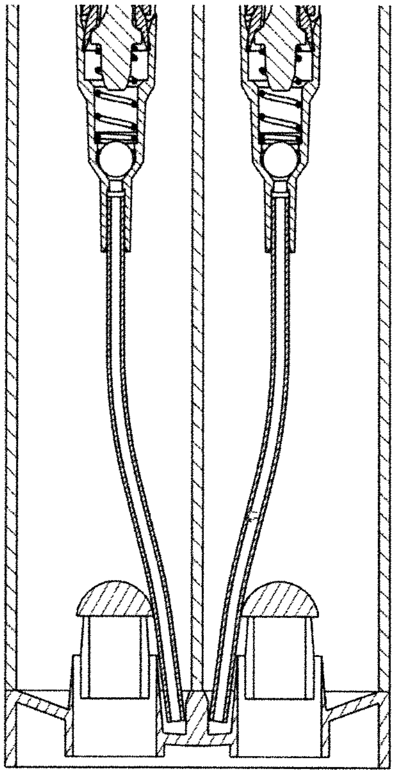

FIG. 5A illustrates the installation process. The reservoir base component 16 with the already inserted inserts 54 is moved from below onto the main reservoir body 14 with the already installed pump devices 30. The intake tubes 42 thus come into contact with the barrier sections 52 and are displaced to one side by the latter such that the arrangement of the intake tubes 42 according to FIG. 5B finally results.

It can alternatively also be provided that the reservoir base component 16 is already fastened on the main reservoir body 14 before the installation of the pump devices 30, for example by press-fitting, welding or adhesive bonding, and that, when the pump devices 30 with the intake tubes 42 already attached thereto are inserted, the barrier sections 52 correspondingly push the intake tubes to one side.

Figure 5C:
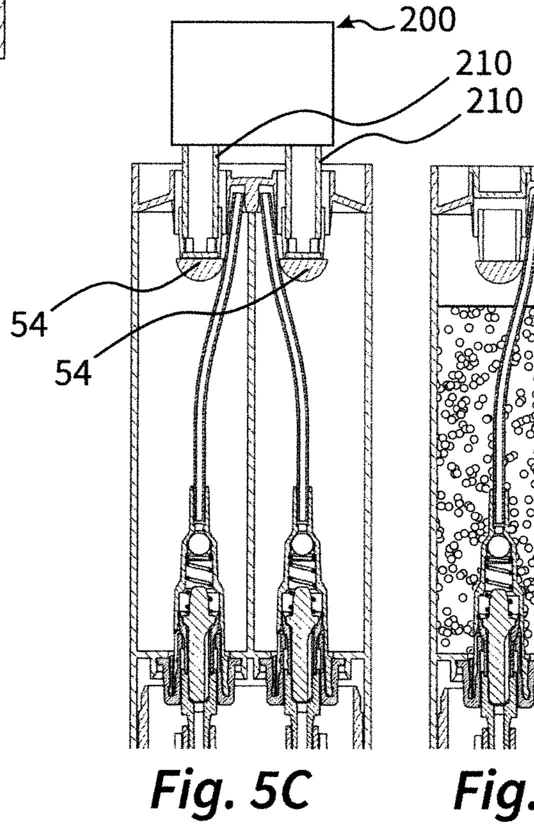
Figure 5D:
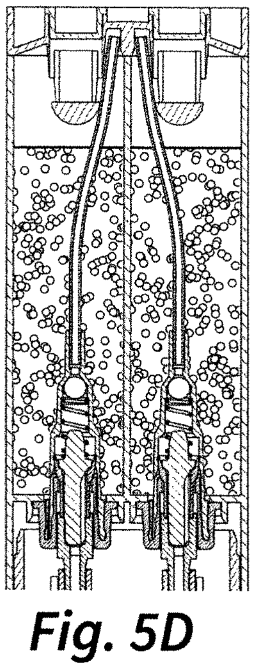

FIGS. 5C and 5D illustrate the filling process. As illustrated in FIG. 5C, two filling nozzles of a filling head 200 again enter the filling openings 60, wherein the inserts 54 arranged here do not interfere with the entrance of the filling nozzles and the introduction of the respective liquids. Alternatively, it can also be provided that the filling nozzles push the inserts 54 into the liquid reservoirs 40 and thus separate them from the reservoir base component 16.

In the design in FIGS. 6A to 6D, the liquid dispenser 10 has the distinctive feature that the liquid reservoirs 40A, 40B are arranged next to each other in an upper region such that they each are delimited by an outer wall 43 of the main reservoir body 14. However, the configuration is different in a lower region in which the filling openings 60A, 60B are also provided. Here, the liquid reservoir 40A surrounds the liquid reservoir 40B. The partition wall 41A, which in the upper part subdivides the cross-section of the main reservoir body 14 centrally into two regions, merges in the lower region of the liquid dispenser 10 into an annular partition wall 41B. As can be seen in FIG. 6A and in particular in FIG. 6B, this results in concentric filling openings 60A and 60B being formed.

FIG. 6C shows the filling process in such a configuration. A filling head 200 is used which has an inner filling nozzle 210A and an outer filling nozzle 210B. An intermediate wall 212 between the respective liquid-guidance regions has an inner shell 212A and an outer shell 212B, wherein, during the filling, the inner shell 212A is arranged inside the partition wall 41B and the outer shell 212B outside the partition wall 41B.

An essential advantage found here is that the rotational position of the liquid dispenser 10 has no relevance during the filling. A complex orienting process can therefore be omitted.

As illustrated in FIG. 6D, the liquid reservoirs 40A, 40B are closed after filling by a common stopper component 70 which has a shape which is adapted to the arrangement of the filling openings 60A, 60B.

Figure 7B:
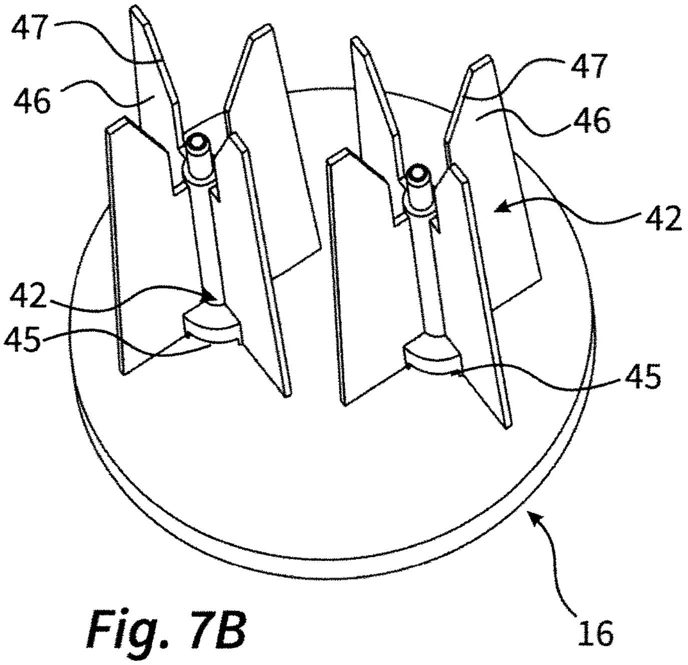
FIGS. 7A to 7D show a liquid dispenser according to a sixth exemplary embodiment of the invention.
Figure 7A:
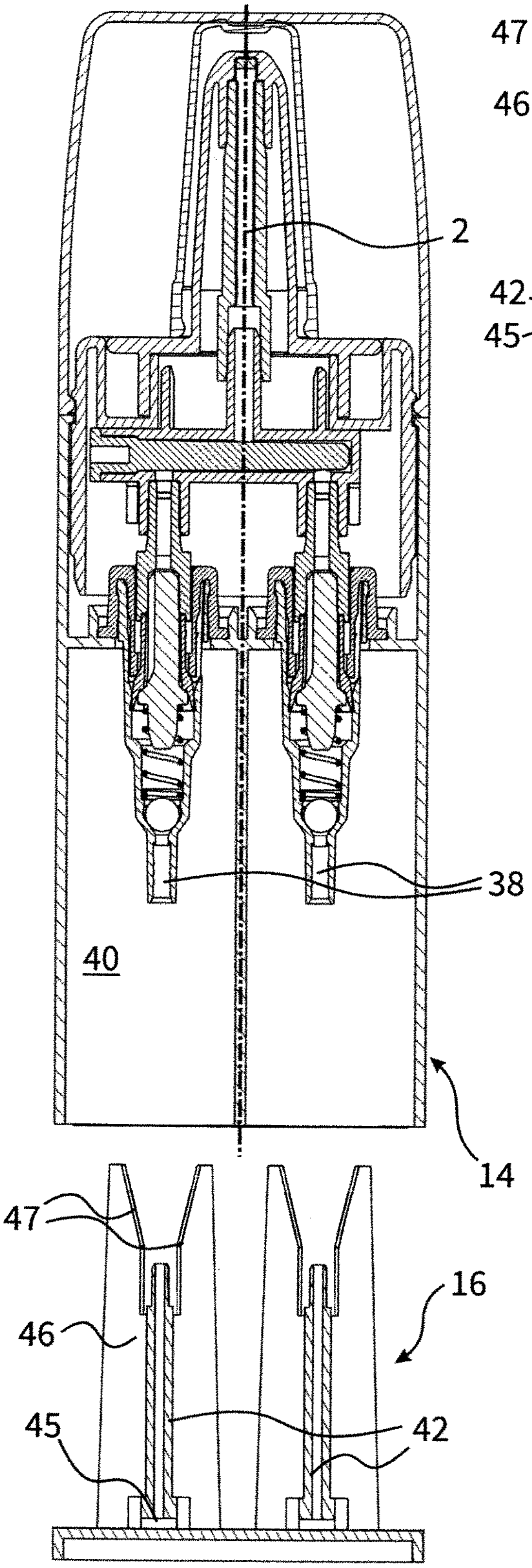

In the design in FIGS. 7A to 7D, a further significantly modified concept is provided. It is provided here that the reservoir base component 16 is already provided with the intake tubes 42 before it is attached to the main reservoir body 14. As can be seen in FIGS. 7A and 7B, these intake tubes are a fixed and preferably integral part of the reservoir base component 16. They have lateral outlets 45 at their bottom end. In order to obtain stability and to simplify installation, they are each provided with four circumferentially distributed individual ribs 46 on which guide surfaces 47, oriented in a funnel shape, are provided.

Figure 7C:
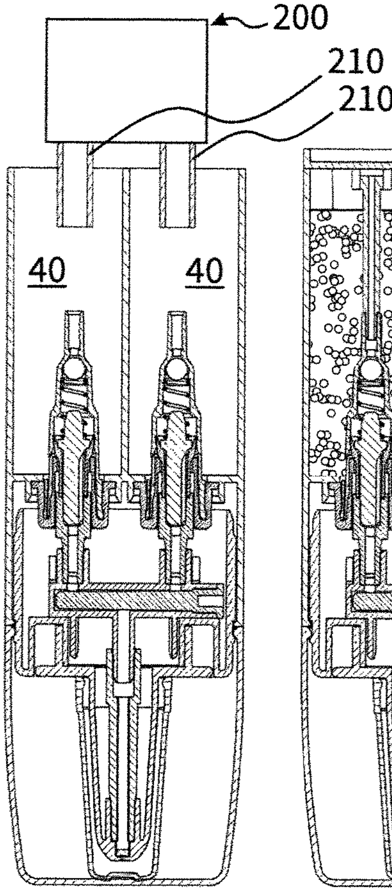
Figure 7D:
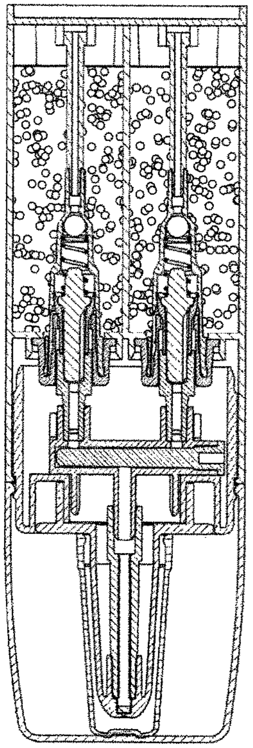

As shown in FIG. 7C, the intake tubes 42 are thus not yet installed at the time of the filling of the liquid reservoirs 40. The liquid reservoirs 40 are first filled with liquid in the manner illustrated in FIG. 7C. Only then is the reservoir base component 16 with the intake tubes 42 connected to the main reservoir body 14, for example, by means of a press-fit connection, an adhesively bonded connection or a welded connection.

Figure 8A:
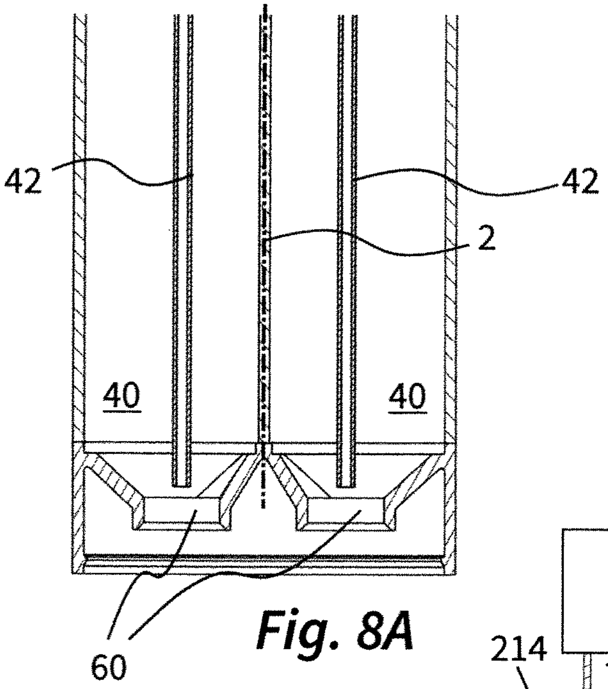
FIGS. 8A to 8D show the filling process of a dispenser with two liquid reservoirs together with a specially designed filling head.
Figure 8B:
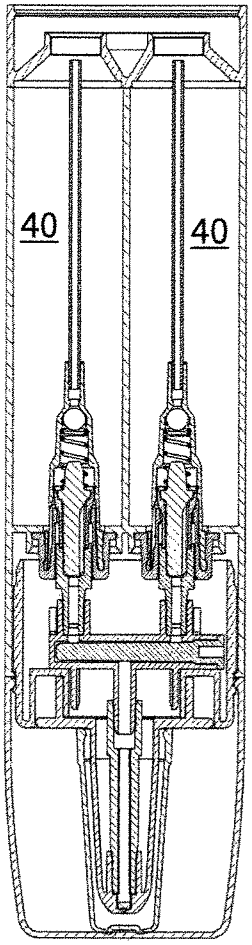
Figure 8C:
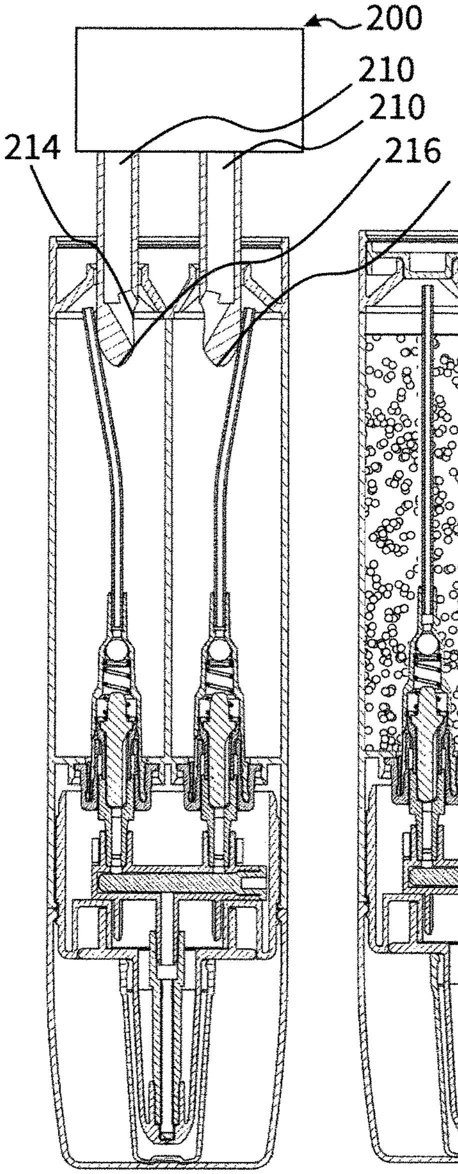
Figure 8D:
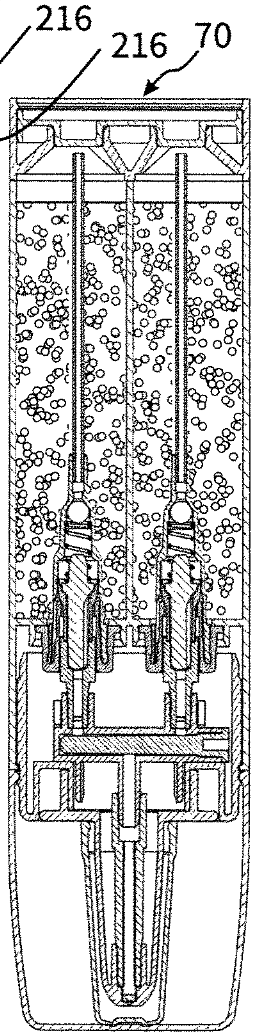

FIGS. 8A to 8D illustrate a further possibility for advantageous filling of the liquid reservoirs 40. In this variant, as illustrated in FIG. 8A, initially there is no guarantee at all that the intake tubes 42 are kept away from the filling openings 60.

However, special filling nozzles 210 are used here. These two filling nozzles 210 are provided at their far end with a displacement geometry 216, in the present case with a tip which tapers downwards with respect to FIG. 8C. When these filling nozzles 210 enter the filling openings 60, in so doing they push the intake tubes 42 to one side. The liquid reservoirs 40 are then filled via outlet openings 214 provided on the sides of the filling nozzles 210. As soon as the filling is finished, the filling openings are closed via a common stopper component 70 in the already described fashion.

The invention claimed is:

1. A liquid dispenser for dispensing a cosmetic or pharmaceutical liquid produced by mixing at least two starting liquids, comprising:

a reservoir body having an interior;

a partition wall disposed within the interior of the reservoir body;

at least two liquid reservoirs housed within the reservoir body for respectively holding the starting liquids, the liquid reservoirs extending in a main direction of extent of the liquid dispenser and being separated from each other by the partition wall;

at least one discharge opening;

at least one pump device for delivering liquid from the liquid reservoirs to the discharge opening;

a respective intake opening for removing the liquid, via the at least one pump device, disposed at a top end of each of the liquid reservoirs;

a respective intake tube extending from the intake opening to a bottom end of each of the liquid reservoirs; and a reservoir base attached to the main body and having a first component defining therein a respective filling opening disposed at the bottom end of each of the liquid reservoirs, the reservoir base comprising barrier elements inside the respective liquid reservoirs in alignment with the respective filling openings and disposed to block the respective filling openings and prevent the respective intake tubes from entering the filling openings during an installation of the reservoir base onto the reservoir body in an installation direction, the barrier elements comprising respective second components of the reservoir base, the second components comprising respective inserts, the inserts being separate from the first component of the reservoir base and being fastened to the first component, each of the inserts having, on an upward facing side thereof at least one guide surface, the guide surfaces being disposed and configured to deflect the respective intake tubes away from the respective filling openings during installation of the reservoir base onto the reservoir body in the installation direction, the guide surfaces each having a shape deviating from a planar shape or a planar shape oblique relative to the main direction of extent.

2. The liquid dispenser according to claim 1, wherein the guide surfaces are oriented obliquely to the main direction of extent of the liquid dispenser.

3. A liquid dispenser for dispensing a cosmetic or pharmaceutical liquid produced by mixing at least two starting liquids, comprising:

at least two liquid reservoirs for holding the starting liquids, wherein the liquid reservoirs extend in a main direction of extent of the liquid dispenser and are separated from one another by a partition wall;

at least one discharge opening and at least one pump device by which liquid can be delivered from the liquid reservoirs to the discharge opening;

a respective intake opening for removing the liquid via the at least one pump device disposed at a top end of each of the liquid reservoirs;

a respective intake tube extending from the intake opening to a bottom end of each liquid reservoir; and a respective filling opening provided in a base region at the bottom end of each of the liquid reservoirs, wherein at least in the base region, situated opposite the at least one pump device of the liquid reservoir, a second of the two liquid reservoirs surrounds a first of the two liquid reservoirs, and the partition wall is formed in the base region as an annular partition wall surrounding a first filling opening of the first liquid reservoir, the annular partition wall being surrounded by a second filling opening of the second liquid reservoir.

4. The liquid dispenser according to claim 3, wherein at least in an upper region of the liquid reservoirs, the liquid reservoirs are arranged next to each other such that the liquid reservoirs each adjoin a common outer wall and a non-annular partition wall originating from the outer wall, and the liquid dispenser further includes a transfer wall structure between the base region and the upper region, the transfer wall structure merging the non-annular partition wall into the annular partition wall.

5. The liquid dispenser according to claim 1, further comprising:

two pump devices each associated with one of the liquid reservoirs; and a push actuator displaceable relative to the liquid reservoirs, the pump devices being configured to deliver liquid from the liquid reservoirs to the discharge opening by displacement of the push actuator relative to the liquid reservoirs.

6. A method for producing and filling a liquid dispenser with two liquid reservoirs, the method comprising:

providing a liquid dispenser with a main reservoir body, at least one intake tube and a reservoir base component having two filling openings each provided in a base region of the respective liquid reservoirs;

attaching the reservoir base component to the main reservoir body;

pushing the at least one intake tube away from at least one of the filling openings with the reservoir base component during the step of attaching;

thereafter filling the liquid reservoirs while the liquid dispenser is oriented so that the filling openings face upwards; and carrying out the filling with at least one filling head having at least two filling nozzles entering the filling openings simultaneously or one after the other and dispensing liquid there and hence filling the liquid reservoirs.

7. The liquid dispenser according to claim 1, wherein the guide surfaces each have a tapered shape.

* * * * *